United States Patent
Usami et al.

(10) Patent No.: US 11,617,764 B2
(45) Date of Patent: *Apr. 4, 2023

(54) PERITONEAL DIALYSIS FLUID

(71) Applicant: TERUMO KABUSHIKI KAISHA, Tokyo (JP)

(72) Inventors: Hirokazu Usami, Yamanashi (JP); Yoshihiko Koyama, Yamanashi (JP); Hiroshi Nishitani, Yamanashi (JP); Tsuyoshi Ariizumi, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1318 days.

This patent is subject to a terminal disclaimer.

(21) Appl. No.: 16/018,582

(22) Filed: Jun. 26, 2018

(65) Prior Publication Data

US 2018/0296593 A1   Oct. 18, 2018

Related U.S. Application Data

(62) Division of application No. 14/435,362, filed as application No. PCT/JP2012/080625 on Nov. 27, 2012, now Pat. No. 10,010,563.

(51) Int. Cl.
   *A61K 33/14*    (2006.01)
   *A61K 31/718*   (2006.01)
   *A61M 1/28*     (2006.01)
   *A61J 1/20*     (2006.01)
   *A61J 1/10*     (2006.01)

(52) U.S. Cl.
   CPC ............ *A61K 33/14* (2013.01); *A61K 31/718* (2013.01); *A61M 1/287* (2013.01); *A61J 1/10* (2013.01); *A61J 1/202* (2015.05); *A61J 1/2093* (2013.01)

(58) Field of Classification Search
   CPC ..... A61K 33/14; A61K 31/718; A61M 1/287; A61M 1/28; A61M 1/159
   See application file for complete search history.

(56) References Cited

U.S. PATENT DOCUMENTS

| | | | |
|---|---|---|---|
| 5,827,820 A | 10/1998 | Dumoulin et al. | |
| 10,010,563 B2 * | 7/2018 | Usami | A61P 13/12 |
| 11,020,420 B2 * | 6/2021 | Nakamoto | A61K 31/715 |
| 2004/0060865 A1 | 4/2004 | Callan et al. | |
| 2004/0089604 A1 | 5/2004 | Zimmeck | |
| 2004/0121982 A1 * | 6/2004 | Martis | A61K 31/724 514/58 |
| 2006/0128658 A1 | 6/2006 | Martis et al. | |
| 2015/0231321 A1 | 8/2015 | Nishitani et al. | |

FOREIGN PATENT DOCUMENTS

| | | | |
|---|---|---|---|
| EP | 1008341 A | 6/2000 | |
| JP | 2000-051348 A | 2/2000 | |
| JP | 2006-513211 A | 4/2006 | |
| JP | 2007-524629 A | 8/2007 | |
| JP | 2010-150281 A | 7/2010 | |
| WO | WO 2005/002599 A1 | 1/2005 | |
| WO | WO-2011081660 A1 * | 7/2011 | ........... A61K 31/198 |

OTHER PUBLICATIONS

The extended European Search Report dated Jul. 24, 2018, by the European Patent Office in corresponding European Patent No. 18163628.3-1112. (7 pages).
International Search Report (PCT/ISA/210) dated Feb. 5, 2013, by the Japanese Patent Office as the International Searching Authority for International Application No. PCT/JP2012/080625.
Extended European Search Report dated Apr. 12, 2016, issued by the European Patent Office in corresponding European Application No. EP 12889157.9-1466/2926835 (7 pages).
Communication Pursuant to Article 94(3) EPC issued by the European Patent Office in corresponding European Patent Application No. 12889157.9-1466 dated Nov. 8, 2017 (4 pages).

* cited by examiner

*Primary Examiner* — Michael B. Pallay
(74) *Attorney, Agent, or Firm* — Buchanan Ingersoll & Rooney PC

(57) ABSTRACT

The present invention is a sterile peritoneal dialysis fluid, including an acidic first liquid containing 60.0 to 94.0 g/L of icodextrin and 0 to 2.34 g/L of sodium chloride, and an alkaline second liquid containing an alkaline pH regulator, in which the first liquid after sterilization has a pH of 5.0 to 5.5, the second liquid after sterilization has a pH of 6.5 to 7.5, and a mixture of the first liquid and the second liquid after sterilization has a pH of 6.0 to 7.5. The present invention can provide a peritoneal dialysis fluid containing icodextrin, in which the stability of icodextrin during the heat sterilization and the subsequent storage can be improved to the maximum, and the pH of the peritoneal dialysis fluid is close to the physiological range.

10 Claims, No Drawings

PERITONEAL DIALYSIS FLUID

CROSS-REFERENCE TO RELATED APPLICATIONS

This application is a divisional application of U.S. patent application Ser. No. 14/435,362, filed Apr. 13, 2015, which is a national stage filing under § 371 of International Application No. PCT/JP2012/080625, filed Nov. 27, 2012, the entireties of which aforementioned applications are incorporated herein by reference.

TECHNICAL FIELD

The present invention relates to a peritoneal dialysis fluid containing icodextrin.

BACKGROUND ART

A peritoneal dialysis therapy which is one of the symptomatic therapies for renal failure has attracted attention as one of home medical cares, since the device and implement do not become large in scale as compared with a dialysis therapy performed through an artificial kidney and also there are few temporal restrictions. Many of currently-used peritoneal dialysis fluids use glucose as an osmotic agent. Glucose has an advantage of being relatively safe, and being inexpensive; however, a continuous dehydration effect cannot be obtained because glucose has a small molecular weight and is rapidly absorbed from the peritoneum. From the above situation, an investigation of an osmotic agent that can maintain ultrafiltration during long-term storage in place of glucose was performed, and it has been found that icodextrin, a glucose polymer, is suitable for a peritoneal dialysis fluid.

Icodextrin is not rapidly absorbed via the peritoneum due to a large molecular weight, and acts mainly as a colloid osmotic agent, and a dehydration effect can be obtained while maintaining the osmotic pressure with blood plasma. Currently, in a peritoneal dialysis fluid in which icodextrin is used, a medical solution is prescribed to be in the range of pH 5.0 to 5.5 in order to prevent the decomposition and coloring of the icodextrin.

According to a recent study, it has been reported that a peritoneal dialysis fluid having such a pH substantially lowers the immunological defense mechanism for a peritoneal macrophage, and increases the risk of peritonitis against the ingress of bacteria. Furthermore, it has been reported that in a peritoneal dialysis fluid of pH 5.0 to 5.5, damage to cultured peritoneal mesothelial cells is significantly high, and it is effective for reducing the damage that the pH of the peritoneal dialysis fluid is 6.5 or more.

However, the pH of a peritoneal dialysis fluid has a significant impact on the stability of icodextrin; when the pH is increased without changes, the icodextrin is decomposed into glucose at the time of manufacture or storage, the peritoneal dialysis fluid is colored by the deterioration of the glucose, and then the product value is significantly lowered. That is, the absorbance of 284 nm, which is an index of 5-hydroxymethylfurfural which is a main decomposition product of glucose, is successively increased.

Therefore, as a method of increasing the pH of the peritoneal dialysis fluid while suppressing the decomposition and coloring of the icodextrin, a pharmaceutical preparation has been developed, in which an icodextrin and a liquid medicine component having high pH are separately stored until a time for use and are aseptically mixed immediately before use (Patent Literature 1).

However, requirement for the stability of peritoneal dialysis fluid and the safety of peritoneal dialysis fluid increasingly becomes high-dimensional in recent years, and a development of a stable peritoneal dialysis fluid has been desired, in which a pH is in the physiological range which does not affect on human bodies, and the decomposition of icodextrin into glucose and the coloring of icodextrin are suitably suppressed.

CITATION LIST

Patent Literatures

Patent Literature 1: Japanese Patent Application Laid-Open No. 2010-150281

SUMMARY OF INVENTION

Technical Problem

The present invention is to provide a peritoneal dialysis fluid, in which the stability of icodextrin during the heat sterilization and the subsequent storage is improved to the maximum, and the pH of the peritoneal dialysis fluid is close to the physiological range.

Solution to Problem

The problems described above are achieved according to the following present invention.
(1) The present invention is a sterile peritoneal dialysis fluid, comprising an acidic first liquid containing 60.0 to 94.0 g/L of icodextrin and 0 to 2.34 g/L of sodium chloride, and an alkaline second liquid containing an alkaline pH regulator, in which the first liquid after sterilization has a pH of 5.0 to 5.5, the second liquid after sterilization has a pH of 6.5 to 7.5, and a mixture of the first liquid and the second liquid after sterilization has a pH of 6.0 to 7.5.
(2) The present invention is the peritoneal dialysis fluid described in the above (1), in which the first liquid contains neither lactic acid nor a lactate. Herein, examples of the lactate include sodium lactate, potassium lactate, and calcium lactate.
(3) The present invention is the peritoneal dialysis fluid described in the above (1) or (2), in which the alkaline pH regulator in the second liquid contains at least one of sodium hydroxide and sodium hydrogen carbonate.
(4) The present invention is the peritoneal dialysis fluid described in any one of the above (1) to (3), in which the second liquid contains at least one of sodium chloride, lactic acid, sodium lactate, calcium chloride, and magnesium chloride.
(5) The present invention is the peritoneal dialysis fluid described in any one of the above (1) to (4) being stored in a medical bag body, in which the bag body has a first chamber and a second chamber which are formed by separation of the inner part by a openable partition means, the first chamber having a discharge port for communicating inside and outside the bag body, the first liquid being stored in the first chamber, and the second liquid being stored in the second chamber.

Advantageous Effects of Invention

In the peritoneal dialysis fluid of the present invention, successive increase of the absorbance at 284 nm of the peritoneal dialysis fluid can be suppressed by the separate storage of the component of the peritoneal dialysis fluid containing icodextrin and the component of the alkaline peritoneal dialysis fluid, particularly lactic acid and a lactate; namely, the glucose decomposition products of icodextrin during the heat sterilization and the subsequent storage were largely suppressed, and the peritoneal dialysis fluid excellent in stability can be provided.

DESCRIPTION OF EMBODIMENTS

Hereinafter, a peritoneal dialysis fluid of the present invention will be described in detail. The peritoneal dialysis fluid of the present invention mainly comprises a first liquid containing icodextrin and a second liquid containing an alkaline pH regulator without containing icodextrin, in which the peritoneal dialysis fluid is a two-component peritoneal dialysis fluid where the first liquid and the second liquid are mixed immediately before use, and the peritoneal dialysis fluid has a pH of 6.0 to 7.5 after the mixture.

In the present invention, the content of the icodextrin in the first liquid is 60.0 to 94.0 g/L, preferably 65.0 to 85.0 g/L. In a case where the content of the icodextrin is less than 60.0 g/L, the osmotic pressure after the mixture of the first liquid and the second liquid is too low, and sufficient dialysis cannot be expected, and in a case where the content of the icodextrin contained in the first liquid exceeds 94.0 g/L, it is not preferable because the content of the glucose decomposition products becomes large. That is, according to this, the glucose decomposition products of icodextrin during the heat sterilization and the subsequent storage can be suitably suppressed, and the peritoneal dialysis liquid stable and excellent in preserving property can be achieved.

The content of sodium chloride in the first liquid is 0 to 2.34 g/L, preferably 1.78 to 2.15 g/L. The sodium chloride is incorporated for the purpose of adjusting the osmotic pressure, and when the content of sodium chloride in the first liquid exceeds 2.34 g/L, it is not preferable because the content of the glucose decomposition products becomes large.

The pH of the first liquid after sterilization is in an acidic region; specifically, it is preferable in the range of pH 4.7 to 5.5, and more preferable in the range of pH 5.0 to 5.5. When the pH is less than 4.7 or more than pH 5.5, it is not preferable because the content of the glucose decomposition products becomes large.

In addition, as needed, the pH adjustment may be performed, for example, by using hydrochloric acid, lactic acid, and the like.

Furthermore, in the present invention, the second liquid comprises at least one of sodium hydroxide and sodium hydrogen carbonate as an alkaline pH regulator. The content of the alkaline pH regulator is an amount required to adjust the pH of the peritoneal dialysis liquid to pH 6.0 to 7.5, preferably pH 6.5 to 7.5 after the first liquid and second liquid after sterilization are mixed with the addition of at least one of a lactate and lactic acid incorporated as an alkalizing agent.

In the peritoneal dialysis fluid of the present invention, when the pH after the mixture is less than 6.0, the immunological protection mechanism of macrophage is lowered and damage to peritoneal mesothelial cells is high, and when the pH exceeds 7.5, an adverse effect on living bodies is concerned.

The present invention comprises at least one of a lactate and lactic acid incorporated as an alkalizing agent, and the content is not particularly limited, may be the same amount contained in an ordinary peritoneal dialysis fluid as a lactate ion, and it is preferably 30 to 45 mEq/L as a lactate ion after the mixture. The alkalizing agent may be contained in any one of the first liquid and the second liquid; however, it is preferably incorporated into the second liquid not containing icodextrin in view of the stability of the peritoneal dialysis fluid, for example, the suppression of the degradation of the icodextrin to glucose and the suppression of the degradation of the glucose. Examples of the lactate include sodium lactate, potassium lactate, and calcium lactate, and preferably sodium lactate.

The peritoneal dialysis fluid of the present invention, in addition to the components above, comprises various components contained in an ordinary peritoneal dialysis fluid, i.e., a sodium ion, a calcium ion, a magnesium ion, a chloride ion, and the like. These contents may be the same amount contained in an ordinary peritoneal dialysis fluid, and it is preferable that the sodium ion is 100 to 200 mEq/L, the calcium ion is 0 to 5 mEq/L, the magnesium ion is 0 to 5 mEq/L, and the chloride ion is 50 to 180 mEq/L after the mixture of the first liquid and the second liquid.

The components above may be contained in any one of the first liquid and the second liquid; however, they are preferably incorporated into the second liquid not containing icodextrin in view of the stability of the peritoneal dialysis fluid. Furthermore, these components may be incorporated into the peritoneal dialysis fluid of the present invention as lactic acid, sodium lactate, sodium chloride, calcium chloride, magnesium chloride, and the like in the same manner as in an ordinary peritoneal dialysis fluid.

In the peritoneal dialysis fluid of the present invention, the first liquid and the second liquid are filled and packed separately into a container made of polypropylene, polyvinyl chloride, or the like, and sterilized, and then the first liquid and the second liquid are aseptically mixed immediately before use.

In particular, the peritoneal dialysis fluid of the present invention is preferably separated into the first liquid and the second liquid and stored in a medical bag body having a first chamber and a second chamber which are formed by separation of the inner part by a openable partition means, in which the first chamber has a discharge port for communicating inside and outside the medical bag body. In this case, it is preferable that the first liquid is stored in the first chamber, and the second liquid is stored in the second chamber. According to this, even in a case where the first liquid and the second liquid are administered without mixing by any chance, the first liquid which is osmotically relatively safe can be administered.

Examples of the openable partition means include a heat seal which is able to be fractured by the liquid pressure of the stored first liquid or second liquid when one of the first chamber and the second chamber is pressed. According to this, the first liquid and the second liquid can be easily mixed. Specific examples of the medical bag body include a container of MIDPELIQ (registered trademark) (manufactured by TERUMO CORPORATION).

In the present invention, examples of the sterilization method include autoclave sterilization (high-pressure steam sterilization), and the conditions are preferably at 110 to 140° C. for 5 to 50 minutes, and specifically at 121° C. for 30 minutes.

The peritoneal dialysis fluid of the present invention is described in detail in the above; however, the present invention is not limited to the above, various improvements and changes may be made without departing from the scope of the invention.

EXAMPLES

Hereinafter, the present invention will be described in more detail with reference to specific examples of the present invention. However, the present invention should not be limited to the following Examples.

Example 1

75 g of icodextrin was dissolved into 840 mL of water for injection, and a first liquid was prepared. Furthermore, 5.35 g of sodium chloride, 4.48 g of sodium lactate, 0.257 g of calcium chloride, and 0.051 g of magnesium chloride hexahydrate were dissolved into 160 mL of water for injection, the pH was adjusted by sodium hydroxide, and a second liquid was prepared. 840 mL of the first liquid and 160 mL of the second liquid were respectively filled into a double-chamber container made of polypropylene (a container of MIDPELIQ (registered trademark) (manufactured by TERUMO CORPORATION)), and then the container was put in a three-side sealed bag made of polypropylene/nylon/polypropylene and was deaeration-packaged. After that, heat sterilization (at 121° C. for 30 minutes) was performed by using an autoclave, and then each pH of the first liquid, the second liquid, and a mixture (peritoneal dialysis fluid) was measured. The pH of the first liquid was 5.1, the pH of the second liquid was 7.0, and the pH of the mixture was 6.6.

Example 2

75 g of icodextrin and 1.87 g of sodium chloride were dissolved into 840 mL of water for injection, and a first liquid was prepared. Furthermore, 3.48 g of sodium chloride, 4.48 g of sodium lactate, 0.257 g of calcium chloride, and 0.051 g of magnesium chloride hexahydrate were dissolved into 160 mL of water for injection, the pH was adjusted by sodium hydroxide, and a second liquid was prepared. 840 mL of the first liquid and 160 mL of the second liquid were filled, and heat sterilized under the same conditions as those in Example 1, and then each pH of the first liquid, the second liquid, and a mixture (peritoneal dialysis fluid) was measured. The pH of the first liquid was 5.1, the pH of the second liquid was 7.0, and the pH of the mixture was 6.6.

Comparative Example 1

75 g of icodextrin and 4.48 g of sodium lactate were dissolved into 840 mL of water for injection, and a first liquid was prepared. Furthermore, 5.35 g of sodium chloride, 0.257 g of calcium chloride dihydrate, and 0.051 g of magnesium chloride hexahydrate were dissolved into 160 mL of water for injection, and the pH was adjusted by sodium hydroxide, and a second liquid was prepared. 840 mL of the first liquid and 160 mL of the second liquid were filled, and heat sterilized under the same conditions as those in Example 1, and then each pH of the first liquid, the second liquid, and a mixture (peritoneal dialysis fluid) was measured. The pH of the first liquid was 5.4, the pH of the second liquid was 6.9, and the pH of the mixture was 6.6.

Comparative Example 2

75 g of icodextrin, 5.35 g of sodium chloride, 18.3 g of calcium chloride dihydrate, 5.08 g of magnesium chloride hexahydrate, and 4.48 g of sodium lactate were dissolved into 1000 mL of water for injection and prepared. 1000 mL of the prepared liquid was filled into a single-chamber container made of polypropylene, and then the container was put in a three-side sealed bag made of polypropylene/nylon/polypropylene and was deaeration-packaged. After that, heat sterilization (at 121° C. for 30 minutes) was performed by using an autoclave, and then the pH of the obtained peritoneal dialysis fluid was measured. The pH was 4.3.

Comparative Example 3

100 g of icodextrin was dissolved into 840 mL of water for injection, and a first liquid was prepared. Furthermore, 5.35 g of sodium chloride, 4.48 g of sodium lactate, 0.257 g of calcium chloride, and 0.051 g of magnesium chloride hexahydrate were dissolved into 160 mL of water for injection, the pH was adjusted by sodium hydroxide, and a second liquid was prepared. 840 mL of the first liquid and 160 mL of the second liquid were filled, and heat sterilized under the same conditions as those in Example 1, and then each pH of the first liquid, the second liquid, and a mixture (peritoneal dialysis fluid) was measured. The pH of the first liquid was 4.3, the pH of the second liquid was 7.2, and the pH of the mixture was 6.2.

(Time-Dependent Change Test)

As to the peritoneal dialysis fluids in Examples 1 and 2, and Comparative Examples 1 to 3, time-dependent changes of the absorbance of 284 nm, which is an index of 5-hydroxymethylfurfural which is amainde composition product of glucose, were measured. The results are shown in Tables 1 and 2. Furthermore, the peritoneal dialysis fluids in Examples 1 and 2, and Comparative Examples 1 to 3 were stored in a thermostat bath at 60° C., and the mixture of the first liquid and the second liquid (except for Comparative Example 2) was performed immediately before the measurement of absorbance.

TABLE 1

|  | Example 1 | Example 2 |
| --- | --- | --- |
| Day 0 | 0.087 | 0.089 |
| Day 3 | 0.107 | 0.115 |
| Day 5 | 0.120 | 0.125 |
| Day 7 | 0.141 | 0.147 |

TABLE 2

|  | Comparative Example 1 | Comparative Example 2 | Comparative Example 3 |
| --- | --- | --- | --- |
| Day 0 | 0.102 | 0.107 | 0.133 |
| Day 3 | 0.121 | 0.244 | 0.155 |
| Day 5 | 0.132 | 0.368 | 0.289 |
| Day 7 | 0.154 | 0.455 | 0.334 |

As shown in Tables 1 and 2, in the peritoneal dialysis fluid of the present invention, a peritoneal dialysis fluid having an absorbance of 284 nm of less than 0.15 can be achieved after heat sterilization or even after storing for 7 days at 60° C. by performing appropriate heat sterilization. This could not have been predicted from a conventional art.

INDUSTRIAL APPLICABILITY

That is, as described in detail, the peritoneal dialysis fluid of the present invention can make the pH to be in the physiological range, maximally suppresses the decomposition of icodextrin during the heat sterilization and the subsequent storage, and thus can be industrially applicable as the peritoneal dialysis fluid highly excellent in the stability.

The invention claimed is:

1. A sterile peritoneal dialysis fluid, comprising:
an acidic first liquid containing 60.0 to 89.3 g/L of icodextrin and 0 to 2.34 g/L of sodium chloride, and
an alkaline second liquid containing an alkaline pH regulator,
wherein a mixture of the first liquid and the second liquid after sterilization has a pH of 6.0 to 7.5.

2. The peritoneal dialysis fluid according to claim 1, wherein the alkaline pH regulator in the second liquid comprises at least one of sodium hydroxide and sodium hydrogen carbonate.

3. The peritoneal dialysis fluid according to claim 1, wherein the second liquid comprises at least one of sodium chloride, lactic acid, sodium lactate, calcium chloride and magnesium chloride.

4. The peritoneal dialysis fluid according to claim 1, the first liquid containing 65.0 to 85.0 g/L: of icodextrin.

5. The peritoneal dialysis fluid according to claim 1, the first liquid containing 1.78 to 2.34 g/L of sodium chloride.

6. The peritoneal dialysis fluid according to claim 1, the first liquid containing 1.78 to 2.15 g/L of sodium chloride.

7. The peritoneal dialysis fluid according to claim 1, wherein the mixture of the first liquid and the second liquid after sterilization has a pH of 6.5 to 7.5.

8. The peritoneal dialysis fluid according to claim 1, wherein the alkaline regulator comprises at least one compound selected from the group consisting of a lactate and lactic acid.

9. The peritoneal dialysis fluid according to claim 1, wherein the mixture of the first liquid and the second liquid comprises 100 to 200 mEq/L of sodium ion, 0 to 5 mEq/L, of calcium ion, 0 to 5 mEq/L, of magnesium ion, and 50 to 180 mEq/L, of chloride ion.

10. The peritoneal dialysis fluid according to claim 1, wherein the second liquid after sterilization has a pH of 7.0 to 7.5.

* * * * *